United States Patent [19]

St. Phillips

[11] Patent Number: 4,933,525

[45] Date of Patent: Jun. 12, 1990

[54] MICROWAVEABLE CONTAINER HAVING TEMPERATURE INDICATING MEANS

[75] Inventor: Eric A. St. Phillips, Fairport, N.Y.

[73] Assignee: Mobil Oil Corporation, New York, N.Y.

[21] Appl. No.: 327,654

[22] Filed: Mar. 22, 1989

[51] Int. Cl.⁵ .................. H05B 6/80; G01K 11/16
[52] U.S. Cl. .................. 219/10.55 E; 219/10.55 F;
219/506; 426/88; 426/243; 116/216; 374/161;
374/149
[58] Field of Search ................ 219/10.55 E, 10.55 B,
219/10.55 F, 10.55 R, 506; 426/88, 107, 241,
243; 374/159, 160, 161, 162, 149, 141; 116/216,
219; 99/DIG. 14

[56] References Cited

U.S. PATENT DOCUMENTS

| | | | |
|---|---|---|---|
| 3,594,126 | 7/1971 | Fergason et al. | 426/88 |
| 3,704,625 | 12/1972 | Seto et al. | 374/162 |
| 3,782,195 | 1/1974 | Meek et al. | 116/216 X |
| 3,991,615 | 11/1976 | Hornung | 219/10.55 R |
| 4,065,655 | 12/1977 | Wong et al. | 219/10.55 D |
| 4,335,181 | 6/1982 | Marano, Jr. et al. | 426/107 |
| 4,341,937 | 7/1982 | Staats | 219/10.55 M |
| 4,410,493 | 10/1983 | Joslyn | 426/88 X |
| 4,428,321 | 1/1984 | Arens | 426/88 X |
| 4,786,773 | 11/1988 | Keefer | 219/10.55 E |

FOREIGN PATENT DOCUMENTS

WO87/00274  1/1987  PCT Int'l Appl. ............... 116/216

Primary Examiner—Philip H. Leung
Attorney, Agent, or Firm—Alexander J. McKillop; Charles J. Speciale; Michael J. Mlotkowski

[57] ABSTRACT

A reusable microwaveable container having a temperature indicator mounted permanently to the side walls of the container. The temperature indicator is a liquid crystal film display device having a plurality of display devices which indicate various temperature levels. The liquid crystal films change color in response to a preset temperature such that each display changes color at incrementally increasing temperatures. The displays are reversible in that they return to their original color as the temperature decreases. Alternately, or additionally, the temperature sensing indicator may be provided on a closure lid which fits over the container, so that the temperature may be detected from steam rising from the food being cooked or heated.

16 Claims, 2 Drawing Sheets

MICROWAVEABLE CONTAINER HAVING TEMPERATURE INDICATING MEANS

BACKGROUND OF THE INVENTION

1. Field of the Invention

The present invention relates to a microwaveable container, and more particularly, to a container constructed of microwave-transparent material for the heating or cooking of foods through the intermediary of microwave energy, wherein the container is equipped with a temperature indicating arrangement which represents a change in the temperature prevalent within the container through a visual color change evidenced in a temperature sensitive liquid crystal film.

In recent years, there has been a significant increase in the popularity of microwave ovens for the cooking and/or reheating of a large variety of foods in a quick and efficient manner. Microwave energy heats food directly by heating the moisture content of the food so as to, in turn, heat the food itself; and therefore, it has been necessary to develop containers or receptacles which are microwave-transparent so that the microwaves unimpededly reach the entire surface areas of the food contained within the oven. This phenomenon has led to the development of reusable microwaveable containers which have gained in popularity in serving both as food storage and cooking or heating vessels. The reusability of these containers is an important feature with regard to their practicality in the employment thereof in microwave ovens.

Microwave ovens vary in size and also in power levels such that cooking times for similar types of foods considerably differ from one oven model to another. Furthermore, different kinds of foods require varying lengths of microwave cooking time in order for the foods to reach to desired degree of doneness or heating in relation to their serving temperature. Presently, a consumer cooking, heating, defrosting or reheating foods in a microwave oven must rely on a trial-and-error method to determine whether or not the food is done to the desired temperature; and possibly stop the oven operating and either taste or feel the food to generally ascertain the temperature level thereof. Because some foods; for example, such as popcorn, heat very efficiently and rapidly in a microwave oven, it is very easy to unintentionally overheat or overcook them.

Visual indications of heat, such as steam or bubbling of liquids due to excessive temperatures, are usually not efficient indicators of cooking time in a microwave oven, since microwave ovens are equipped with microwave energy reflecting screens which ordinarily cover the viewing window on the oven door so as to prevent any leakage of radiation. The screens form a mesh which obscures any detailed viewing of the food chamber within the microwave oven and; consequently, the oven must be opened and the food removed for visual or physical inspection to determine the doneness thereof. This leads to a very inefficient heating or cooking of the food, since the excitation of the moisture molecules within the food must be repeated once the food is returned to the oven in order to continue heating or cooking. Although various measures have been undertaken in the microwave cooking technology in order to provide a visual indication of cooking temperature and/or cooking doneness, such visual indicators are deficient; for example, due to a lack of reusability, inconvenient positioning in relation to the food, as well as contributing to the overall cost of the microwave oven, thereby rendering these devices expensive and impractical to use.

2. Discussion of the Prior Art

In the prior art, there are disclosed several types of temperature sensitive indicators for completion of cooking or heating cycles for use in microwave ovens; however, wherein the indicators are inconvenient in use and are subject to drawbacks which can adversely affect the cooking time, as well as substantially increasing the cost of the oven.

Wong, et al. U.S. Pat. No. 4,065,655 disclose a microwave leakage indicator for microwave ovens, wherein the indicator consists of a strip of encapsulated liquid-crystal film which is mounted on a backing constituted from microwave-absorbing material. The strip of liquid-crystal film and the microwave-absorbing material are positioned on and secured to the edge of the microwave oven door so as to overlap the slot between the door and the frame of the oven. In the presence of microwaves, i.e. in the event of any leakage, the microwave-absorbing material generates heat which quickly changes the color of the liquid crystal film material to indicate the existence of leakage of harmful radiation. This device is not employable as a temperature indicator or sensor inside the cooking chamber of the microwave oven, since the presence of microwaves triggers the heat generation in the microwave-absorbing material to change the color of the liquid crystal film. This device would not be useful as a temperature indicating means, because the color change would occur as soon as the oven is turned on and there are present microwaves.

Hornung U.S. Pat. No. 3,991,615 discloses a coaxial cable-connected temperature-sensing probe which is embedded into the food load in order to measure the internal temperature of the food. The coaxial cable connects to a jack on the wall of the cooking chamber of the oven, and circuitry is provided to turn the oven off when the probe reaches a preset temperature which is sensed by thermistors arranged within the tip of the probe. Wiring is provided to connect the thermistor to the coaxial cable and then to the circuitry which controls the oven. A reflector-type handle is provided to ensure that the probe does not disrupt the microwave pattern within the cooking chamber. A temperature indicating means of this type is subject to the drawback that proper temperature indication can only be achieved for food loads which must be penetrated by the probe. Accordingly, this device is inconvenient for the measurements of the temperature of liquids, dispersed items such as fruits and vegetables, or for the reheating of various foods enclosed in a single or closed container. Additionally, this probe and its associated circuitry will, of necessity, increase the overall cost of the microwave oven.

Staats U.S. Pat. No. 4,341,937 describes a microwave oven having a support shelf which supports a food load at an intermediate region or raised level within the cooking cavity of the oven. An electromagnetic field sensor is located opposite a probe antenna such that the intermediate region where the food load is supported is interposed between the antenna and the sensor. The sensed electromagnetic field strength provides a sensitive measure of the amount of microwave energy not absorbed by the food load but which flows around and/or through the food. The sensed electromagnetic field strength provides an indication of conditions within the food being cooked, particularly as to the moisture content of the food. The progress of cooking in the microwave oven is monitored by this arrangement; however, this apparatus represents an elaborate and expensive system for determining the cooking progress. Furthermore, the food load must be located beneath the antenna in order to provide accurate temperature indications.

In addition, several other types of cooking progress or cooking doneness indicators are presently being marketed for use on containers to be placed in microwave ovens. One such indicator is manufactured by the Armour Corporation, which provides a container having a liquid crystal display which changes color in response to the heat generated within the container by the food. This indicator is permanently attached to the container and is not reusable, thereby rendering the container impractical if the temperature indicator is required for repeated usage. Once the color changes, the indicator is non-reusable since the display never returns to its original color.

Other known indicators include two types manufactured by Omega Corporation, most notably the model R5 strip type indicator and the series of RRN models. The model R5 indicators comprise a strip of five different color temperature bands covering a range of 50° to 70° C. in 5° C. increments. These adhesive backed strips may be applied to various surfaces and are temperature-reversible such that, as the temperature increases, the color changes for various temperature levels, and as the temperature decreases, the bands revert to their original colors. The RRN models are circular labels which may be attached to various surfaces, and also change color as the temperature increases and revert to their original color as the temperature decreases. A disadvantage of these type of indicators lies in the type of adhesive and the over-laminations required to both secure the labels to various surfaces and to provide reusability with regard to washing and overheating. The adhesive must be strong enough to prevent loosening during overheating and washing conditions, yet must be thin enough to allow for accurate temperature measurement. Furthermore, the adhesive must be compatible with the surfaces on which the label would be used so as not to peel off inadvertently.

SUMMARY OF THE INVENTION

In order to ameliorate or obviate the shortcomings and limitations encountered in prior art microwaveable containers and temperature indicators which are adapted for sensing the temperature and cooking progress of food being heated or cooked in a microwave oven, the present invention is directed to the provision of a simple and inexpensive container structure constituted from a microwave-transparent material, and which is equipped with an integral, non-removable reversible temperature indicating arrangement providing an accurate indication over the cooking progress of the food in the container. The container incorporates a bottom and a side wall structure which is integral with and extends upwardly from the bottom, wherein the side wall is provided with a permanently affixed temperature indicting arrangement which is temperature-reversible and which, resultingly allows the container to be reusable in conjunction with the indicator. The indicating arrangement may consist of a separate device which is permanently secured to the wall of the container structure, but is preferably embedded into the side wall structure so as to be integral with the container.

Moreover, pursuant to another aspect of the invention, the container contemplates the provision of a separate closure lid, essentially consisting of a domed structure which is mountable on the container base and is provided with the temperature indicating arrangement permanently affixed thereto. This embodiment provides more accurate indication of the cooking progress since steam generated by the food during the heating thereof will rise and be detected by the temperature indicating arrangement on the closure lid. Preferably, both the closure lid and the container itself may be provided with temperature indicating means, enabling the container to be inventively employed without a closure lid. Additionally, it is contemplated that several temperature indicating devices be arranged about the periphery of the container such that the temperature indicating arrangement may be readily viewed by a person irrespective of the orientation of the container within the cooking chamber in the microwave oven.

Accordingly, it is a primary object of the present invention to provide a microwaveable container which is equipped with a novel temperature indicating device which allows a user to monitor a cooking progress in order to determine when foods being cooked or heated in a microwave oven have reached a temperature indicative of doneness of the foods.

Another object of the invention is to provide a microwaveable container having a temperature indicating device which can be readily viewed from the outside of the oven irrespective of the orientation of the container within the oven chamber.

Yet another object of the invention is to provide a container having a closure lid which fits securely over the container, and wherein the closure lid is equipped with a temperature indicating device which indicates to a user when the food being cooked or heated is din a state of doneness.

It is a further object of the invention to provide a microwaveable container having temperature and indicating arrangement which is reusable in that the temperature indicating arrangement changes color in response to a temperature increase and reverts to its original color in response to a temperature decrease.

It is a still further object to provide a microwaveable container in which a reuseable temperature indicating arrangements are permanently affixed to the container and to the closure lid.

BRIEF DESCRIPTION OF THE DRAWINGS

The foregoing and other objects and advantages of the invention may now be more readily ascertained from the following detailed description of an exemplary embodiment of the microwave container having a novel temperature indicating arrangement mounted thereon, taken in conjunction with the accompanying drawings; in which.

DETAILED DESCRIPTION OF THE PREFERRED EMBODIMENTS

Figure 1:
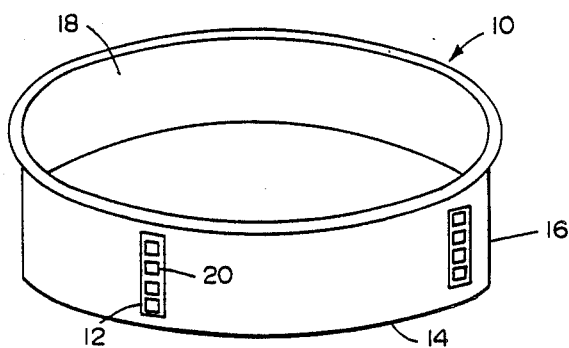
FIG. 1 illustrates a perspective view of the microwaveable container with a temperature indicator pursuant to the present invention.

Referring now in specific detail to the drawings, in which the same reference numerals refer to similar or identical elements throughout the several views, FIG. 1 shows a microwaveable container 10 which is provided with a temperature indicating sensing arrangement 12 pursuant to the present invention. Container 10 is generally bowl-shaped, having a bottom 14 and side wall structure 16 integral with the bottom 14 and extending upwardly therefrom. The geometrical shape of container 10 is not essential to the invention; any suitable shape, such as circular, square, rectangular, etc., may be readily employed, provided the container includes a side wall structure 16. Side wall structure 16 together with the bottom 14 defines the food-receiving interior 18 of the bowl-shaped container 10.

Side wall structure 16 is provided with at least one temperature indicator arrangement, generally designated by reference numeral 12. Preferably, indicator arrangements 12 are located at various points spaced about the outer periphery of side wall structure 16, so that a user employing the container 10 for cooking or heating foods in a microwave oven (not shown) may readily view at least one indicator irrespective of the orientation of the container 10 within the oven chamber. As shown, indicator 12, which is discussed in detail hereinbelow, generally consists of a strip or array of temperature indicating sensors which change in color responsive to an increase or decrease in temperature.

Figure 3:
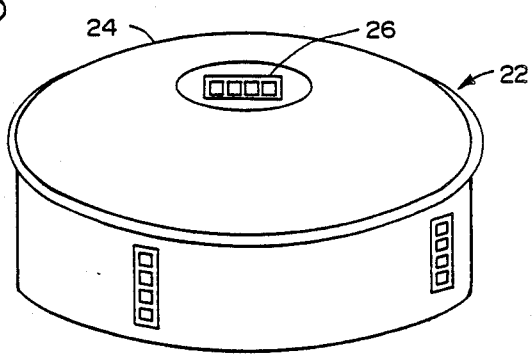
FIG. 3 illustrates a perspective view of an alternate embodiment of the present invention showing a container and closure lid arrangement.

FIG. 3 illustrates an alternate embodiment of the container 10, wherein a container base 22 is provided for holding a food load, and a closure lid 24 is supported on base 22 so as to cover the food and prevent it from splattering during heating. Closure lid 24 can be of any suitable shape, and preferably forms a dome or has a shape similar to the base container 22. In FIG. 3 a temperature indicator 26 is shown as being provided on closure lid 24. Temperature indicator 26 is similar to indicator 12 shown in FIG. 1, and may be provided alone or in combination with an indicator 12 on the container. For shallow containers, indicator 26 is very useful in affording the user a good overview angle since the viewing window of a microwave oven is generally elevated above the bottom of the oven cooking chamber.

Figure 2:
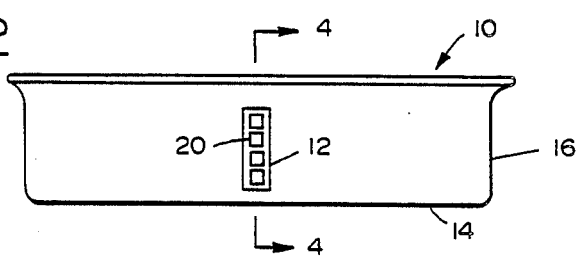
FIG. 2 illustrates a side elevational view of the microwaveable container of FIG. 1.

FIG. 2 illustrates a side view of container 10 and shows temperature indicator arrangement 12 as being equipped with an array of temperature sensors, which comprise temperature sensitive liquid crystal display films 20. These display films 20 each have a predetermined color indicative of a room temperature type. As the temperature increases, the displays change color at a preset temperature and change at increasing incremental temperatures, preferably at 5° C. or 10° C. increments. In this manner, the film display which is preset to the lowest temperature changes color first, the second lowest will change color next as the temperature increases, and so on until indicative that the desired temperature of the food has been reached. Preferably, the size of container 10 dictates that indicator arrangement 12 be positioned in such a manner that food contacts against the inner surface of side wall 16 behind the indicator arrangement 12 so that the temperature of the food is enabled to be sensed directly. Since microwaves heat the food directly, and very little radiant heat would normally be detected by the indicator, it is important that the indicator arrangement 12 be in close proximity to the food load. Therefore, it is preferable to provide a closure lid 24 in which the temperature indicating device 26 is mounted to be located above the food load, so that any steam generated during the cooking process would then provide an accurate indication of temperature since the steam rises and the heat thereof would be sensed by the indicator device 26. The closure lid 24 is conventional in nature, and is preferably provided with steam vents (not shown) to prevent any pressure build-up in the container overpressurization during heating or cooking.

Figure 4:
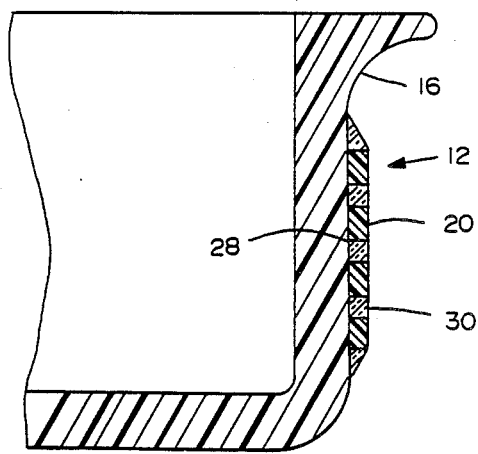
FIG. 4 illustrates a fragmentary sectional view of the microwaveable container of FIG. 1 taken along line 4—4 in FIG. 2.

FIG. 4 illustrates a fragmentary elevational sectional view of FIG. 2 taken along line 4—4 therein, and shows the construction of temperature indicator device 12 as arranged on side wall structure 16 of container 10. Indicator device 12 comprises an array of liquid crystal film displays 20, each corresponding to a different temperature in incrementally rising values. Film 20 is adapted to change colors at a predetermined set temperature and is reversible so that it reverts to its original color as the temperature decreases. This, of course, allows the container, as well as the indicator arrangement, to be reusable, and provides an accurate indication over the progress of heating or cooking based on the food temperature. Indicator device 12 essentially consists of an adhesive-backed substrate 28, liquid crystal layer 20 and a coating layer 30 of a protective nature wherein all three layers are preferably laminated and secured to the outer surface of side wall structure 16. Layer 30 is preferably transparent so as to facilitate viewing of the color change of displays 20 by a user. Any suitable adhesive may be employed to secure substrate 28 to the side wall structure 16, and preferably, the adhesive is resistant to excess temperatures as well as to water and detergents so that the container may be easily cleaned through washing.

Figure 5:
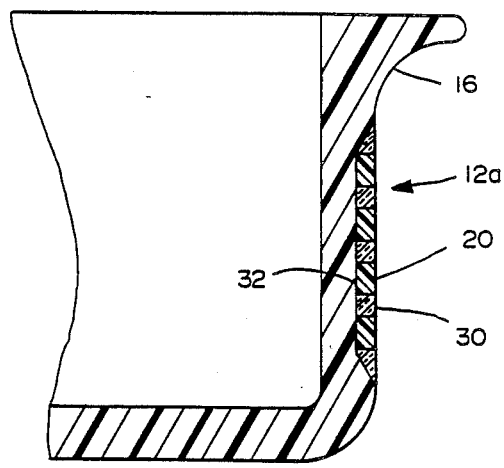
FIG. 5 illustrates a modified embodiment of the temperature indicating device of the present invention as shown in FIG. 4, taken along line 4—4 in FIG. 2.

FIG. 5 illustrates a preferred construction of the temperature sensing indicator 12a. Indicator 12a is shown as being constructed integrally with wall structure 16 in which an indentation 32 is provided wherein there is arranged the liquid crystal film 20. An outer coating layer 30 is provided thereover, which is in the same plane as wall structure 16 such that the side wall has a continuous surface. In this particular construction, it is important that outer or coating layer 30 be watertight and permanently secured to the side wall structure 16. Additionally, in this embodiment, as well as in the embodiment of FIG. 4, it is preferred that layers 28 and 32 be of a color which contrasts with liquid crystal film displays 20 so as to enhance the visibility in the color change.

From the foregoing, it becomes readily apparent that due to the unique reusable temperature indicator on or in the microwaveable container there is attained a considerable improvement over the containers of the prior art, in that both the container as well as its temperature indicating arrangement are reusable so as to provide accurate indications over the cooking progress relative to the temperature or doneness of the food which is being cooked or heated.

While there has been shown and described what are considered to be a preferred embodiments of the invention, it will, of course, be understood that various modifications and changes in form or detail could readily be made without departing from the spirit of the invention. It is therefore intended that the invention not be limited to the exact form and detail herein shown and described, nor to anything less than the whole of the invention herein disclosed as hereinafter claimed.

What is claimed is:

1. A container for the cooking or heating of foods, said container being constructed of microwave-transparent material and having a bottom and wall structure integrally connected with and extending upwardly from said bottom; and temperature-indicating means on said side wall structure comprising at least one temperature-sensitive liquid crystal film indicator, said indicator having a predetermined temperature sensitivity such that said film undergoes a visible color change at a change from a predetermined initial temperature, each said film indicator consisting of a strip fastened to an exterior surface of the wall structure of said container and having an array of said indicators thereon, said indicator being imparted a visible color change at different incrementally increasing temperatures, said color change being reversible so as to revert said indicator to its original color at said predetermined initial temperature.

2. A container as claimed in claim 1, wherein said film indicator comprises an adhesive-backed strip which is adhesively secured to said side wall structure for visible external indication of a change in temperature within the container or container contents.

3. A container as claimed in claim 1, wherein said temperature indicating means is embedded in said side wall structure so as to be integrally fastened to said container.

4. A container as claimed in claim 1, wherein said side wall structure is provided with a plurality of said temperature indicating means arranged at various locations about said side wall facilitating visual indication of temperature change from the outside irrespective of the orientation of said container within an oven.

5. A container as claimed in claim 1, wherein said temperature indicating means is mounted on a substrate having a contrasting color to enhance the viewing of a color change.

6. A container as claimed in claim 5, wherein said contrasting substrate backing comprises said side wall structure.

7. A container as claimed in claim 1, wherein said indicators each have an identical original color, said indicators each changing to a different color to indicate a different temperature level.

8. A container as claimed in claim 1, wherein said indicators each change colors at 10° C. temperature change increments.

9. A container as claimed in claim 1, wherein said indicators each change color in 5° C. temperature change increments.

10. A container as claimed in claim 1, wherein said container includes with a removable closure lid.

11. A container for cooking or heating of foods, said container being constructed of microwave-transparent material, and having a bottom and an upright side wall structure integrally connected with and extending upwardly from said bottom, and a removable closure lid; at least one temperature indicating means on said closure lid comprising a strip having at least one temperature-sensitive liquid crystal film indicator thereon, said indicator being imparted a visible color change at different incrementally increasing temperatures, and said color change being reversible to change said indicator back to an original color in response to a decrease in the temperature.

12. A container as claimed in claim 11, wherein said temperature indicating means comprises an adhesive backed strip for securing said indicating means to said closure lid.

13. A container as claimed in claim 11, wherein said temperature indicating means is embedded in said closure lid to form a permanent component of said lid.

14. A container as claimed in claim 11, comprising an array of said indicators on said strip, said indicators each being imparted a visible color change which is reversible to change said indicators back to an original color as the temperature decreases.

15. A container as claimed in claim 11, wherein said temperature indicating means is mounted on a substrate of a contrasting color to enhance the visibility in the color of said indicator to a user.

16. A container as claimed in claim 15, wherein the surface of said closure lid provides a contrasting background.

* * * * *